United States Patent [19]

Goldman

[11] Patent Number: 5,981,291

[45] Date of Patent: Nov. 9, 1999

[54] ESTROGEN MARKER SYSTEM

[76] Inventor: Dorothee Goldman, 3503 Shepherd St., Chevy Chase, Md. 20815

[21] Appl. No.: 08/855,590

[22] Filed: May 13, 1997

Related U.S. Application Data

[63] Continuation of application No. 08/408,966, Mar. 23, 1995, abandoned.

[51] Int. Cl.$^6$ .......................... G01N 21/77; G01N 33/53; G01N 33/48; G01N 21/00

[52] U.S. Cl. .......................... 436/169; 435/805; 435/806; 435/970; 436/63; 436/64; 436/65; 436/164; 436/169; 436/817; 436/906

[58] Field of Search ..................... 435/805, 806, 435/970; 436/65, 63, 64, 164, 169, 817, 906

[56] References Cited

U.S. PATENT DOCUMENTS

| | | |
|---|---|---|
| 4,320,009 | 3/1982 | Hilton et al. . |
| 4,358,288 | 11/1982 | Goldman ................................. 436/65 |
| 4,772,554 | 9/1988 | Ax et al. ................................. 435/23 |

FOREIGN PATENT DOCUMENTS

96/29606  9/1996  WIPO .

OTHER PUBLICATIONS

Markaverich et al., "Bioflavonoid Interaction With Rat Uterine Type II Binding Sites and Cell Growth Inhibition," Journal of Steroid Biochemistry, 30 (1–6): 71–78, 1988.

Kirkish et al. "Plasma Estriol . . . " Clin. Chem. 24/10, 1830–1832, 1978.

Osawa et al. "Studies on Phenolic Steroids . . . " Steroids 15/1 73–88, 1970.

*Primary Examiner*—Christopher L. Chin
*Assistant Examiner*—Ja-Na A. Hines
*Attorney, Agent, or Firm*—Liniak, Berenato, Longacre & White,LLC

[57] ABSTRACT

A method for evaluating the solubility capacity of free unbound estrogens in body fluids of animals is described.

20 Claims, 4 Drawing Sheets

ESTROGEN MARKER SYSTEM

This is a continuation of application Ser. No. 08/408,906, now abandoned filed on Mar. 23, 1995.

FIELD OF INVENTION

The present invention is directed to a method for determining the capacity of a body fluid to hold "free" estrogens using a unique marker system that is sensitive to changes in the solubility of estrogens in body fluids. More specifically the present invention is directed to a simple, quick and non-invasive and easy to use system which can monitor changes in the body's capacity to hold "free" estrogens in order to permit for screening and early identification of physiological changes and conditions that are estrogen dependant.

BACKGROUND OF THE INVENTION

Estrogens include a group steroid hormones essential for normal development and for the healthy functioning of the reproductive system. Three of these estrogens include 17β estradiol, estriol, and estrone. Evaluation of "free" estrogen levels can have diagnostic importance in screening for abnormal patterns of changes in estrogen solubility levels such as is observed in the growths of certain estrogen dependent tumors, occurrence of cystic ovaries, and the development of possible endometriosis in the reproductive organs of females. In some female mammals changes in concentration of "free" estrogens are known to occur at the time of implantation and before the onset of parturition. It is also known that "free" estrogen levels vary at different times of the life span of a mammal. During fetal development the concentration of estrogens are known to increase in the third trimester of pregnancy due to increased levels of one estrogen form called estriol which is produced by the adrenal glands of the fetus. Prior to delivery, estrogen levels increase significantly in serum and saliva of different species of pregnant mammals. After delivery, estrogen levels fall rapidly in the mother and babies have low levels of "free" estrogens.

It is also known that estrogen levels increase significantly in girls before they reach puberty. As women age, their ability to produce estrogen decreases after the onset of menopause and "free" estrogen levels reach very low levels between 70 and 80 years. Estrogen levels also fall when ovaries are removed from all animal species.

Certain activities such as excessive sports can also diminish "free" estrogen levels. Some cases of anovulation have chronic higher levels of estrogen but fail to reach peak levels of estrogen concentration and can result in a condition known as cystic ovaries. Also some people do not have the ability to control levels of estrogen and have an abnormal situation like excessive bone growth.

Only a small percentage (1% in human females) of the total estrogens in the body are not chemically bound. These estrogens are called "free" estrogens and are considered to have hormone effects on certain body functions such as those described in the previous paragraphs.

The following chart demonstrates examples of how "free" estrogen levels vary for different species and conditions.

| Species | Amount of total estrogen in serum | The amount of free estrogen in saliva |
| --- | --- | --- |
| Woman who has passed through menopause | 10–30 picograms/ml | 1–3 picograms/ml |
| Boys age 7 | .02 pg/ml | |
| Girl before puberty usually between ages 5 and 8 | .6 pg/ml | 1–2 picograms/ml |
| A woman who is in follicule phase of menstrual cycle and has ovaries | 25–75 picograms/ml | 1–4 picograms/ml |
| A girl at puberty or approaching puberty | 200–900 picograms/ml | 2–9 picograms/ml |
| A woman that will ovulate within four days | 200–900 picograms/ml | 4.5 picograms/ml to 9 picograms/ml |
| A pregnant woman in the first 3 months of pregnancy | 1000 to 5000 picograms/ml | 40–100 picograms/ml |
| A pregnant woman in 2nd trimester of pregnancy | 6000 to 16000 picograms/ml/ml | 50–100 picograms/ml |
| A pregnant woman in the last trimester of pregnancy | 10000 to 40000 picograms/ml | 50–150 picograms/ml |
| Cow in early leutal phase | 3.5 +/− 0.7 pg/ml | Not measured |
| Cow two days before estrus | 5.1 −/− 0.3 pg/ml | Not measured |
| Cow at estrus | 7.1 +/− 0.6 pg/ml | Not measured |

The body has a system to regulate the total amount of "free" estrogens at any given time. An ovulating woman can absorb at least 9 picograms of free estrogen in her saliva. A woman who is about to deliver a baby will be able to absorb at least 200 picograms of "free" estrogen in her saliva. An old woman who is menopausal will have only 1–2 picograms of "free" estrogen in her saliva. In each situation the body is able to recognize when the capacity to have "free" estrogens is reached. Excess estrogens become bound to other components in the body fluids thus preventing these excess estrogens from acting as hormones.

Accordingly, a system that can evaluate whether or not the body has reached its capacity to hold "free" estrogens can have many useful applications and can have considerable clinical value and importance as a tool for screening for various conditions affected by changes in "free" estrogen levels. This is especially true in females. It can be used to evaluate when a body fluid is increasing its capacity to hold "free" estrogens such as is observed in serum and saliva prior to parturition. It can also be used by menopausal women to monitor how the body is absorbing estrogen therapy. It can further evaluate imbalances in "free" estrogen levels such as observed in ovarian cysts. It can track estrogen level changes in the normal development of an individual such as in the last stages of fetal development, the onset of puberty, menopause, and other estrogen dependent events.

Current methods to evaluate estrogen levels often need to separate total estrogens into fractions of bound and unbound estrogens. This process involves a series of complicated analytical procedures that are time consuming and frequently require several hours. Furthermore the instrumentation to accomplish this process needs special facilities that are usually only available in research laboratories, clinics, or hospitals. Additionally, many estrogen assays have limited accuracy and frequently must be repeated many times.

The use of anthocyanins pigments as a fertility evaluation medium is known and is described in U.S. Pat. No. 4,358, 288 to Goldman. This patent describes evaluating fertility in females by contacting a mucin-containing body fluid such as saliva with a fertility evaluation medium comprising an anthocyanin pigment and a substrate which facilitates generation of a color response in this pigment in the presence of a vaginal fluid or substance similar to those found in vaginal fluids. This patent does not, however, suggest that observed color changes in anthocyanin pigments under certain specific conditions can be correlated with the capacity of body fluids to hold free, unbound estrogens and can be used to screen for estrogen dependent physiological changes in the body that do not include fertility evaluation.

It is accordingly an object of the present invention to provide a method to easily and rapidly determine whether or not a given body fluid such as saliva, serum, or interstitial fluid has reached its maximum capacity to hold the "unbound" estrogen in order to assess for changes in certain physiological conditions that are estrogen dependent.

It is another object of the present invention to provide a simple, easy to use, quick marker system for "free" estrogen solubility and methodology which permits identification of changes in the body's capacity to hold "free" estrogens based upon optical properties such as color change.

Yet another object of the invention is to provide a simple yet effective method to quantitatively determine what is the additional capacity for "free" estrogens in a body fluid such as saliva, serum, or interstitial fluids.

SUMMARY OF THE INVENTION

It has now been observed that a simple non-invasive system using anthocyanin pigments can be used to determine whether or not the body has maximum levels of "free" estrogens.

In accordance with one embodiment of this present invention, there is provided a method to identify changes in the capacity to hold "free" estrogens in the body fluids of animals which comprises providing a marker that is sensitive to estrogen solubility, which is an anthocyanin pigment on a substrate that facilitates color change or other optical response in the pigment when contacted with an estrogen containing body fluid such as saliva, serum or interstitial fluid in the presence of dilute solutions of calcium salts.

In accordance with the invention, there is also a system to evaluate the color or other optical properties of anthocyanin pigment that, upon contact with a body fluid, give a color response or other measurable optical response that correlates with the capacity of the body fluid to hold "free" estrogens. This system involves a color response that occurs when saliva or some other body fluid (such as serum or interstitial fluid having pH values between 5.8 and 7.3) are contacted with a defined concentration of certain anthocyanin pigments in the presence of a dilute solution of calcium salts. If maximum levels for "free" estrogen already exist in the body, the anthocyanin pigments will show a strong blue response and any added concentrations of "free" estrogens to this body fluid will cause the blue color to increase in intensity. On the other hand, if the tested body fluid has "free" estrogen concentrations that are very small compared to the capacity of the body fluid to hold "free" estrogen, then the color of the anthocyanin pigment observed is purple and increasing the concentrations of "free" estrogens in this body fluid causes the purple color to immediately fade and become very pale or colorless.

According to another aspect of the present invention one can quantitatively evaluate whether a given sample of body fluid, such as saliva is close to its maximum capacity to hold unbound estrogens, by adding defined amounts of given estrogen such as 17β estradiol and counting how many of these defined units are needed to cause the anthocyanin color response to change from its colorless form to the intense blue form. Body fluid samples that need small amounts of the added estrogen to achieve this color change are close to their limit. Body fluid samples that can absorb large amounts of an added estrogen have larger limits in their capacity to hold "free" estrogens.

The anthocyanin system for evaluating the capacity to hold "free" estrogens in a body fluid has a composition comprising an anthocyanin pigment that is mounted onto a substrate which provides for a color response when this treated substrate comes in contact with body fluids that are at pH values between pH 5.8 and 7.2 and are also in contact with a dilute solution of calcium salt.

According to a further aspect of the present invention there is also provided a kit to evaluate the free estrogen capacity of any given body fluid which includes a substrate such as transparent sheets or strips of glass, acetate, or polyethylene or acrylic or containers or cuvettes made of similar transparent materials that are coated or sprayed with defined concentrations of an anthocyanin pigment, a second component such as a wick made of cotton or cellulose or a molecular sieve that can filter components greater than 20,000 Daltons out of the body fluid, a third component including dilute aqueous solutions of calcium salts preferably in concentrations between $10^{-2}$ to $10^{-}$molar, and a fourth component comprising a color comparison chart for comparing color responses produced in the test to colors provided by the chart that reflect defined levels of maximum capacity for "free" estrogens. The "free" estrogen capacity evaluation kit may optionally include standardized units of a certain estrogen concentration which can be used for a quantitative assay to evaluate the additional capacity of body fluid to hold "free" estrogens, and a final component comprising written instructions in assisting the user on how to use the kit and interpret the results in order to screen for physiological changes that are estrogen dependent.

The present invention provides many advantages over current technology to evaluate changes in unbound "free" estrogen levels in animals. First, it is non-invasive and requires small amounts of sample to register a color change. Second, it is simple and easy to prepare. Third, it is quick and easy to read. Fourth, it is accurate and can identify changes in estrogen capacity within +/−2 picograms of a certain type of estrogen per milliliter.

The anthocyanin estrogen solubility marker method of the present invention offers many benefits to current estrogen evaluation processes. First this method can be done at home, on a farm, or in a zoo using body fluids that can be obtained in a non-invasive manner. Additionally, small samples of body fluid (between 10 microliters and 150 microliters) are sufficient to give accurate results. Furthermore, this method can be done quickly. Saliva can be exposed to the estrogen solubility marker system in less than 30 seconds and immediately a clearly defined color response gives feedback about the body's capacity to hold "free" estrogens. A simple, easy to read, estrogen solubility marker system offers new opportunities to make early screening for many physiological conditions that are estrogen dependant.

Specifically, an estrogen marker system that is sensitive to changes in the solubility of estrogens has practical value in anticipating parturition in livestock and in humans. Frequently, there is a great deal of guess work about whether a pregnant female is in labor or not. Sometimes parturition is induced when it is too early and sometimes it is postponed because not enough information is available to indicate the appropriate time. A simple test that measures one parameter of events that are known to be part of the physiological process involved in parturition can improve the guess work and have diagnostic value as well as help individuals to be better prepared for the actual birthing process.

Also, people who require regular estrogen therapy may have need to monitor whether their estrogen medication is in excess to the levels they already have in their body. Furthermore, certain people may want to know about aging such as how close they are to puberty, or how quickly they are approaching menopause.

Additionally, clinics and research institutions may have need for a practical non-invasive device that allows for quick measurement of maximum levels of free estrogens as a routine diagnostic tool to monitor certain aspects of fetal development or to evaluate certain physiological conditions that are estrogen dependant. A measurement which relies on body fluids such as saliva avoids painful blood samples and cuts down on potential infections and other problems that can develop from measuring estrogen solubility levels from blood samples.

DETAILED DESCRIPTION OF THE INVENTION

Figure 1:
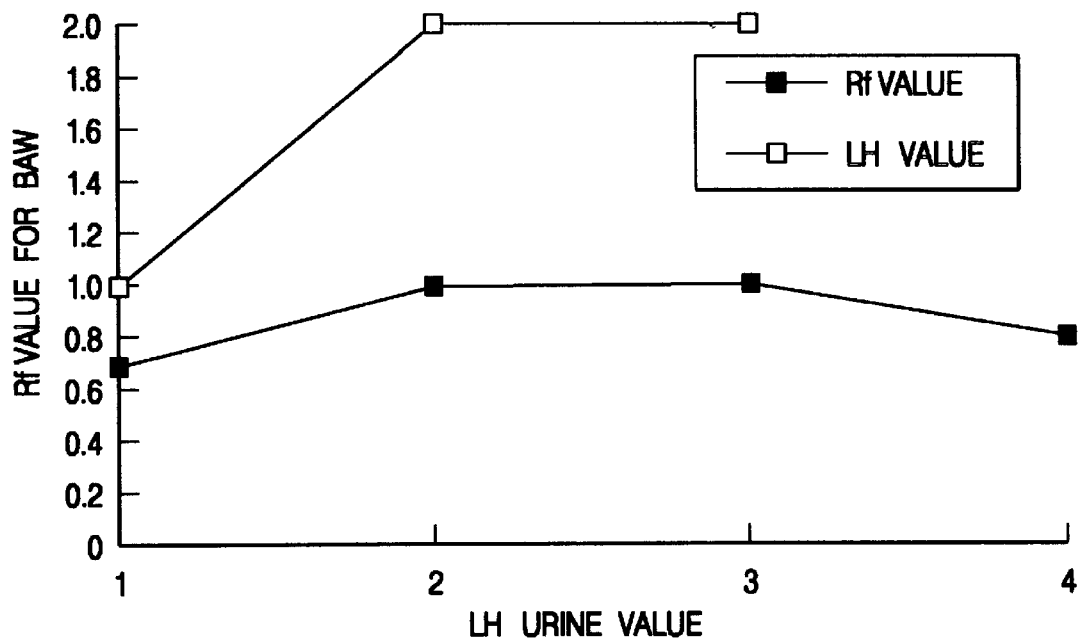
FIG. 1 is a graph illustrating the measurement of Rf values of saliva exposed to anthocyanin pigments extracted from red roses.
Figure 2:
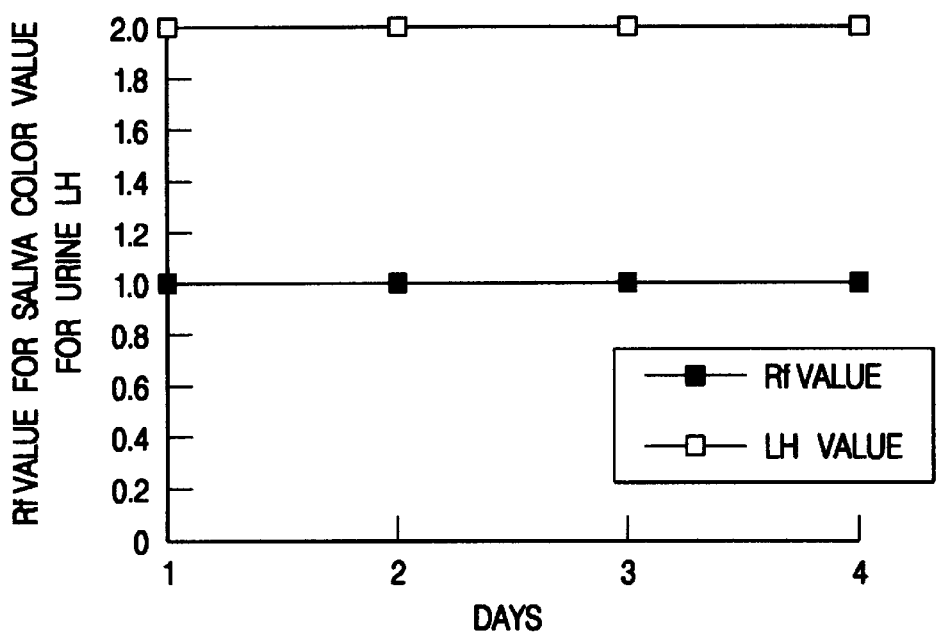
FIG. 2 is a graph similar to that of FIG. 1 for saliva samples taken from a woman one year after her ovaries had been removed.
Figure 3:
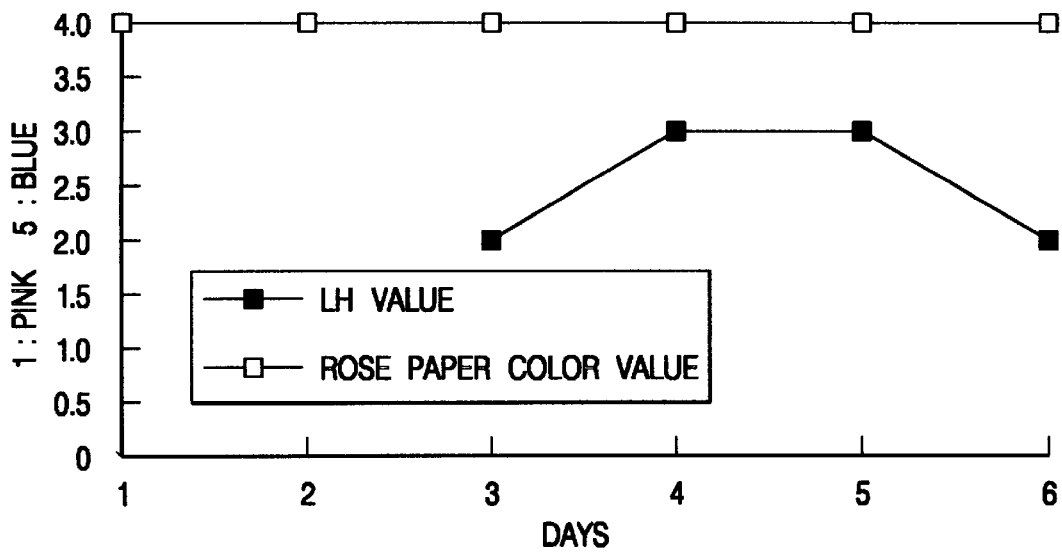
FIG. 3 is a graph comparing color readings on anthocyanins pigments from a woman six weeks after her ovaries had been removed.
Figure 4:
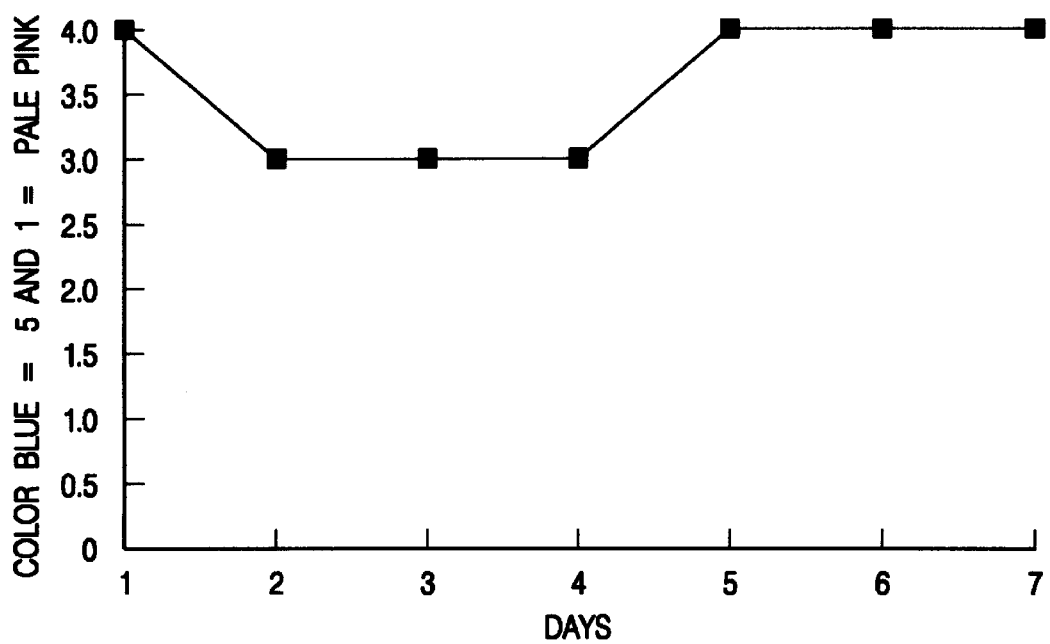
FIG. 4 is a graph illustrating color values of saliva from a woman with no ovaries after having been on estrogen therapy.

The anthocyanins used in the estrogen solubility marker system of the present invention have the following general formula which is based on an equilibrium ratio of two anhydrobase forms of the anthocyanin pigment as they exist at pH vales between 5.5 to 7.5.

In this pH range the pigment structure varies between

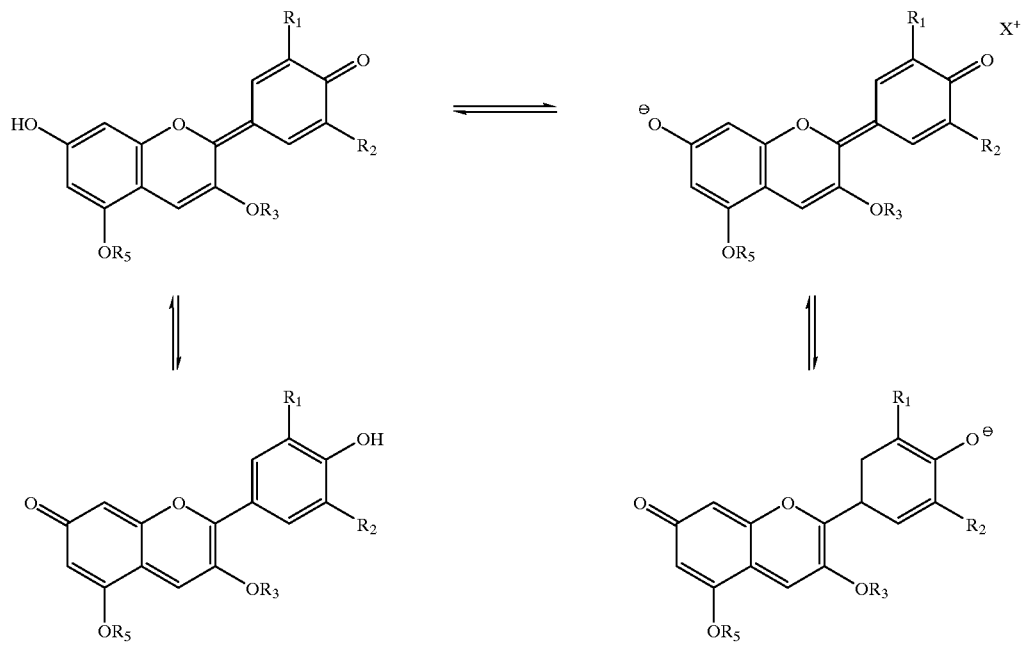

wherein $R_1$ is selected from the group consisting of hydrogen, and $C_1$–$C_4$ alkoxy; $R_2$ is selected from a group consisting of hydrogen, hydroxy, and $C_1$–$C_4$ alkoxy, and $R_3$ is glycoside selected from a group of glucosides and $R_5$ is either a hydrogen or a glycoside selected from the group consisting of glucosides and X is a cation.

The concentration of the pigment must fall within the following ranges. $5 \times 10^{-5}$ molar to $1 \times 10^{-3}$ molar. This range is very important because molar concentrations above $1 \times 10^{-3}$ do not give clear definable results and molar concentrations below $1 \times 10^{-5}$ do not give accurate optical density measurements. At pH levels between 5.8 and 7.2 a molar concentration between $8.0 \times 10^{-5}$ and $2.0 \times 10^{-4}$ gives best results. The tested medium must be between the pH ranges of 5.0 and 7.5 preferably between 5.8 and 7.2. The following form of the anthocyanin pigment is favored in the equilibrium ratio when the "free" estrogen capacity is at its maximum levels.

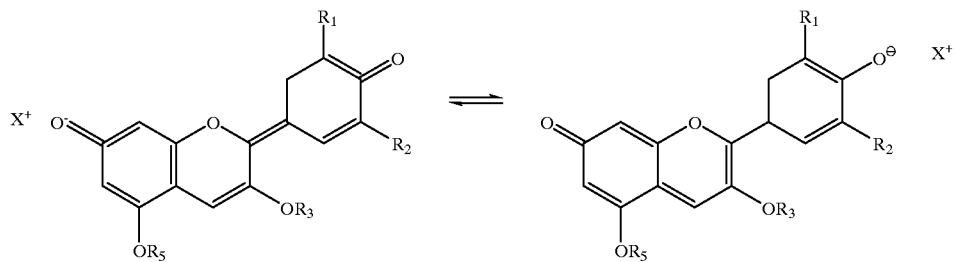

Under these conditions the optical absorbance values are best read between 560 nm and 580 nm. The absorbance values would range between 0.1 and 1.0 for concentrations of anthocyanin pigments between $8\times10^{-5}$ molar and $2\times10^{-4}$ molar and the visible color would be blue or purple depending on the type of anthocyanin pigment used and the actual molar concentration of the pigment.

The following form of the anthocyanin pigment is favored in the equilibrium ratio when the "free" estrogen capacity is not at its maximum levels.

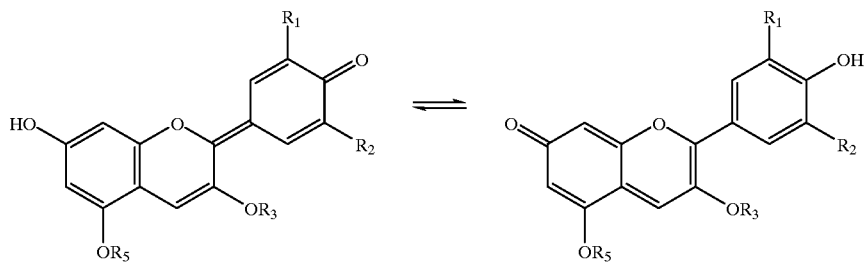

Under these conditions, the absorbance values read between 550 nm and 580 nm. The range of absorbance readings would be below 0.2 and rapidly approach values less than 0.09 and the visible color would range between purple and pale purple or clear.

It is preferred to use anthocyanin pigments that have 3,5 glucosides. Anthocyanin pigments that have a glycoside on the 7 position do not give intelligible results. The preferred anthocyanin for estrogen solubility determination has been documented to be malividin 3,5 diglucoside. Pelagorian 3,5 diglucoside gives good results. Petuidin 3,5 diglucoside also give definable results. Preparations from cyanidin 3,5 diglucoside do not give as well defined results because of the greater instability of cyanidin 3,5 diglucoside in the conditions necessary for these procedures.

In applications of testing this device to date, it has been noted that filtering the saliva samples to include components that have less than 20,000 Daltons gives more definitive results than those samples that have larger components and other foreign objects such as food or microbial organisms. To control for these interferences, it is desirable to put the saliva into a filter or pass it through a membrane that removes the large particles. This process is particularly important in doing optical density measurements.

It should be noted that methods using a visible color evaluation system do not necessarily require this filtering process. Distinguishable color readings can be made in samples of unfiltered body fluids exposed directly to a cotton wick or cellulose strip which is then exposed to a transparent substrate that hold the pigment. When using this method to make a determination for the body's fluid capacity for "free" estrogen levels, it is preferable to perform the following sequence of steps when doing the test with a cellulose or cotton wick:

1. The body fluid that is to be tested should come in contact with the cotton wick or cellulose first.
2. Then the body fluid travels up the wick about 1 mm to 10 mm and the wicked wet body fluid comes in contact with the dried pigment that has been laid onto a non-cellulose transparent surface such as acetate or glass.

This sequence of steps enhances the clarity of the reaction making it easier to distinguish between blue reactions and non-blue color responses.

It is also important to keep the following conditions constant when using the estrogen solubility marking systems. The body fluid should be kept at temperature between 36 and 90 Fahrenheit. This range is important because it has been observed that heating the body fluid over 100 Fahrenheit destroys the ability to evaluate changes.

There are different systems for preparing the substrate:

1. Weighed amounts of dried anthocyanin pigment crystals are placed in small glass tubes or in cuvettes or wells of optical density plates. These plates are packaged in a vacuum and kept out of direct light at temperature that are above freezing and below 150 degrees Fahrenheit.
2. Anthocyanin pigments are prepared in certain molar concentrations in methanol sprayed or painted onto the surface of the plastic or glass to cover a certain surface area in a given period of time.
3. Small plastic beads are coated with anthocyanin pigments and these are placed either behind a piece of cellulose or inside a membrane that separates particles greater than 20,000 Daltons outside and allows for particles less than 20,000 to enter inside the membrane where there is contact with the anthocyanin pigments.

The method to determine if the body fluid contains maximum levels of soluble "free" estrogens involves taking a sample of defined volume of the body fluid and exposing this sample to a given concentration of anthocyanin pigment.

This can be done by using five different techniques.

Method 1. A defined volume of body fluid between 1 microliter and 10 microliters is put onto a piece of chromatographic paper that is in contact with a bead or surface that has 1 microliter to 10 microliters of a given concentration of anthocyanin pigment and this treated chromatographic paper is put into a chromatographic bath and exposed fluid is allowed to migrate up the chromatography paper for a given amount of time. The body fluid comes in contact with the anthocyanin pigment and the combination of the pigment and the body fluid continues migrating with the chromatographic bath fluid up the chromatographic paper at different rates. At the stated time, the exposed chromatographic paper is removed and allowed to dry at room temperature. Then this chromatographic paper is sprayed with a dilute ammonia solution and measurements are made for the distance that the chromatography solution travels. This value is called the Rf value. If the Rf value is greater than 0.4 then the body fluid is approaching its maximum capacity to absorb more "free" estrogens. If the Rf value is from 0.1 to 0.36 then the body fluid is far from it maximum capacity to hold "free" estrogens, as best shown in FIGS. 1 through 4.

Method 2. About 1 microliter to 20 microliters of body fluid sample is exposed to a cotton wick or filter paper that absorbs the body fluid like a wick and this body fluid travels along the wick to a plate that has previously been sprayed or dipped with a given concentration of anthocyanin pigment and then dried at room temperature. When the wet body fluid comes in contact with the dried pigment, a color response is observed that is either dark blue, purple, or clear. If dark blue is observed, the maximum level to absorb estrogen has been reached. If a clear color is observed or a pale pink color is observed, then the body fluid is able to increase its capacity to hold more estrogen.

Figure 5:
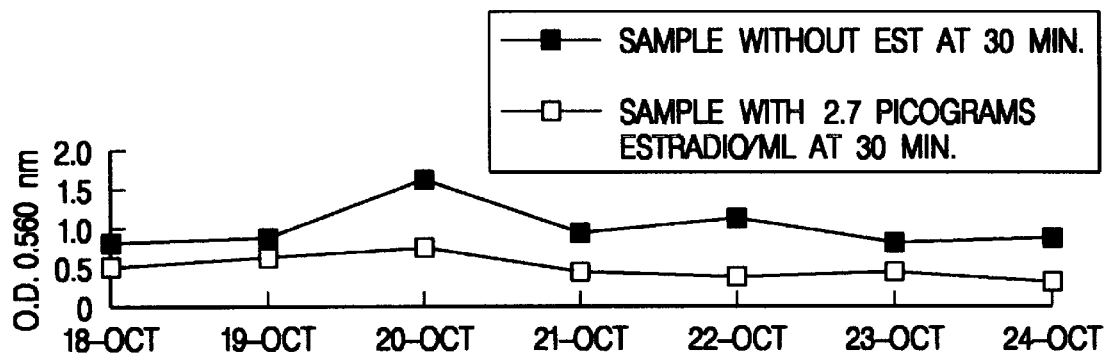
FIG. 5 is a graph illustrating absorbance values for saliva from a woman.

Method 3. One to 3 ml. of body fluid sample is filtered to remove large particles of preferably greater than 20,000 Daltons and 150 microliters suprenatent or filtered sample is put into a container with a liquid preparation of the anthocyanin pigment at a given molar concentration and a color evaluation can be made. If a dark blue color occurs, the sample is near its maximum capacity to hold free estrogen. If little or no color response is observed, the sample has the capacity to absorb more free estrogen. In like manner, these filtered body fluid samples can also be evaluated with a spectrophotometric machine that evaluates optical density at a given wavelength. For example, a molar concentration of an anthocyanin pigment at $2 \times 10^{-4}$ moles/ml that is read at a wavelength of 560 nm, that gives an absorbance value of less than 0.09 means that the capacity to absorb more estrogen is not at its maximal level. An absorbance value for the same molar concentration and read at the same wavelength that is between 1.0 and 2.0 means that the body fluid has maximum level of estrogen capacity and added amounts above a certain concentration of estrogen will result in increased absorbance values as best shown in FIG. 5. An absorbance value between 0.1 and 1.0 means that capacity is somewhere between the maximum level and the minimum level 0.1 being closer to the minimum level and 0.9 being closer to the maximum level).

In interpreting these results one can see that the saliva samples tested with the anthocyanin pigment were all at optical density values that were greater than 0.1 and less that 0.2. According to the interpretation methods of the assay, these values would reflect free estrogen capacity levels that are not at their maximum level. Adding 2.7 pg/ml of free estradiol decreased the optical density in each case indicating that each sample had the capacity to absorb at least an additional 2.7 pg/ml of "free" estradiol.

Method 4. In certain body fluids such as plasma or the saliva of certain animals such as ungulates, it has been observed that it is necessary to add dilute amounts of calcium salts in order to observe these color changes. This method involves mixing the body fluid with the anthocyanin pigment as described in any of the procedures presented above as in steps 1, 2 or 3 and then after the body fluid has been exposed to the anthocyanin pigment according to the prescribed procedure, a defined unit of dilute concentration of $1 \times 10^{-2}$ molar Ca $Cl_2$ or any Ca salt solution is added to this combination. If the resulting color of this procedure is blue or has a high absorbance value as measured in a spectrophotometer, then the body fluid is close to or at its maximum level of "free" estrogen capacity. If the resulting color response is pink than the capacity to absorb more "free" estrogen is not at its maximum level.

| COMPARISON OF HOW CYANIDIN 3,5 DIGLUCOSIDE INTERACTS WITH PLASMA SAMPLES OF THAT HAVE HIGH ESTROGEN LEVELS AND SAMPLES THAT HAVE LOW ESTROGEN LEVEL | | |
|---|---|---|
| | I | II |
| Plasma only | blue | blue |
| Exposure to Ca gluconate | pink | blue |

I. Means that the capacity of plasma to hold "free" estrogen is increasing and the actual concentration of "free" estrogen is low relative to the plasma's total capacity to hold "free" estrogen.
II. Means capacity of the plasma to hold "free" estrogen is approaching its limit and the actual concentration of "free" estrogen is high relative to the plasna's total capacity to hold "free" estrogen.

5. A system to determine what is the additional capacity of the saliva to absorb more "free" estrogen. This can be done by adding given concentrations of "free" estrogens such as a prepared concentration of 17β estradiol and counting how many units of this estradiol concentration are needed to cause the color response to change or the absorbance value to decrease. When the color response turn back to blue or the absorbance value goes up, then the maximum capacity has been reached and the number of units of estradiol need to achieve this state become additional capacity that the body fluid has to absorb more estrogen.

Figure 6:
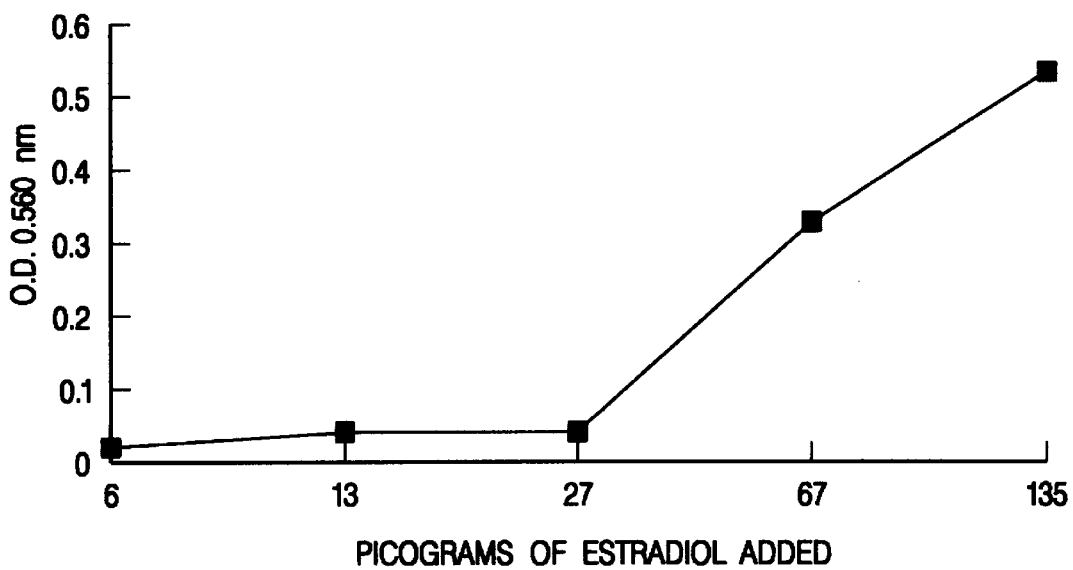
FIG. 6 is a graph illustrating optical density versus estradiol.

FIG. 6 shows how optical density values change for saliva from a 90 year old man who does not have gonads. The initial optical density value for the given concentration of anthocyanin added to saliva sample was 0.303 and the color response was purple. This value indicates that the saliva capacity to hold free estrogen was not at its maximum and not at its minimum. Adding increments of 6 pg/ml of free estradiol up to 27 pg/ml showed a constant decreased-optical density value of about 0.06. When 67 pg/ml estradiol were added, the optical density began to increase and continued to increase up to 135 pg/ml. The decrease in values of added estradiol between 6 and 27 pg/ml indicates that the saliva of this man was able to absorb at least an additional 27 pg/ml of estradiol. In contrast, the increased optical density values observed by the addition of 67 pg/ml of estradiol indicate that this man's saliva could not hold additional "free" estrogens at some value between 27 pg/ml and 67 pg/ml.

When performing this procedure it is important to incubate the given concentrations of estradiol in the saliva before adding the pigment. A reasonable time to incubate the estrogen in the saliva is about 25 minutes. Incubating longer than 1 hour does not change the reaction response. Incubating less than 20 minutes will show proportionally higher values for optical density changes.

Figure 7:
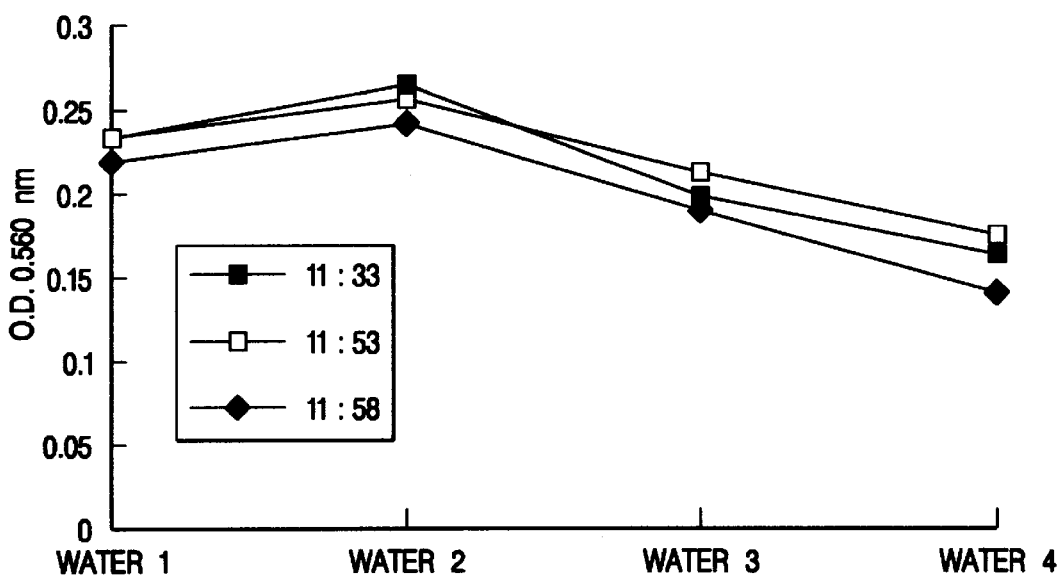
FIG. 7 is a graph illustrating the optical density values for distilled water over time.
Figure 8:
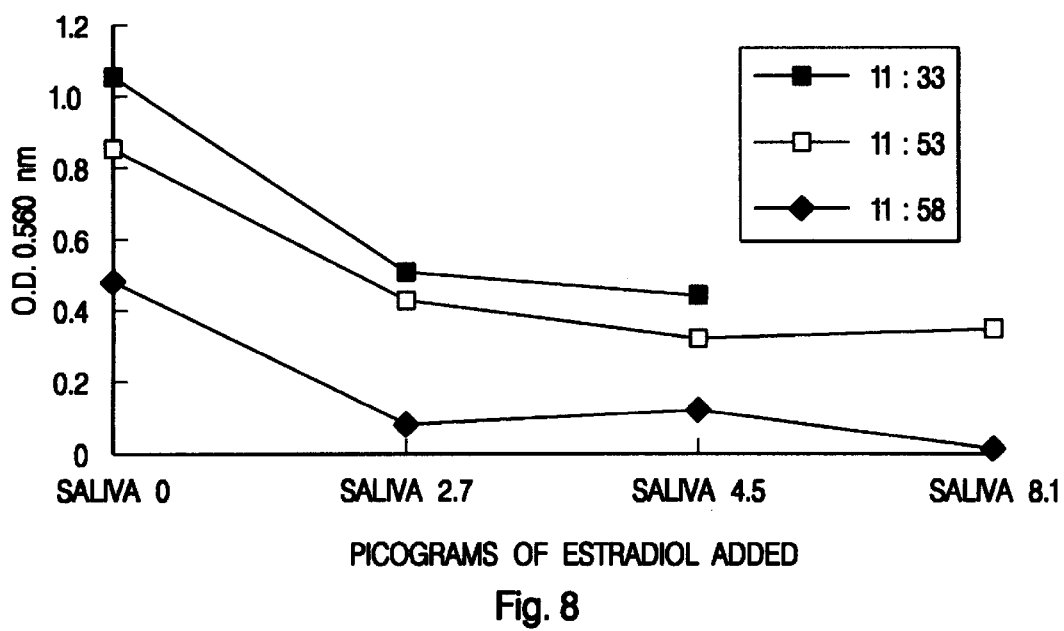
FIG. 8 is a graph comparing optical density values for saliva incubated with estradiol.

It is also important to read the color responses after about 20 minutes after adding the anthocyanin pigment. This is because it takes time for the reaction to stabilize. Waiting more than 1 hour gives less accurate results because the pigment will spontaneously fade when it is in an aqueous medium, as best shown in FIG. 8. However, the degree of fading due to the effect of water is much less than the degree of fading observed when "free" estrogen is added to the body fluid, as best shown in FIG. 7.

The system has demonstrated practical application for prediction of labor in cows and in woman as documented by these observations.

SUMMARY OF COLOR RESPONSES TO SALIVA TESTS ON FIVE COWS BEFORE DELIVERY

|  | Date |  | Color response |
|---|---|---|---|
| Cow #328 |  |  | Saliva exposed to substrate with anthocyanin pigments extracted from rose pigments |
|  | Feb. 14 |  | Pink spot went to blue |
|  | Feb. 15 |  | Pink spot went to blue |
|  | Feb. 17 |  | Pink section then very pale |
|  | Feb. 18 |  | Delivered |
| Cow #329 | Feb. 10 |  | Pale color response |
|  | Feb. 11 |  | Delivered |
| Cow #73 | Feb. 14 |  | Blue - stayed blue |
|  | Feb. 20 |  | Blue - slight pink went back to blue |
|  | Feb. 23 |  | Purple |
|  | Feb. 24 |  | Delivered |
| Cow #80 | Feb. 20 |  | Blue - stayed blue |
|  | Feb. 26 |  | Pink |
|  | Feb. 27 |  | Delivered |
| Cow 860-S | June - | 1 day | Pink |
|  |  | 6 hours | White |
|  |  | 0 hours | Delivered |

PREDICTION OF ONSET OF LABOR

Another application of this invention has been to anticipate the onset of labor in pregnant women. About two weeks prior to delivery in full term pregnancies, there is a color shift in the saliva test as used on the cellulose wick exposed anthocyanins extracted from rose pigments. (During most of pregnancy, the color response is blue or purple blue). Two weeks prior to delivery the color response shifts to pink or no blue. This color response remains until the day labor begins when it shifts to a clear, pale blue response about 6 hours prior to delivery as observed in eight spontaneous deliveries of full term pregnancies. This patter of color changes has also been observed in induced deliveries which were observed to shift from blue to purple within 20 minutes to 2 hours after induction was initiated and then proceed to delivery within 4 to 12 hours after the purple color response was observed.

Spontaneous labor in full term pregnancies

| 1. May 27 | Woman noted dramatic shift from pink to clear white at 2:00 p.m. At 6:00 p.m. mucus plug released and the color response was still clear. The woman went to the hospital and the baby was born that night at 10:00 p.m. |
|---|---|
| 2. Nov. 22 | Woman noted pink responses 18 hours prior to delivery. At 8 hours before birth she noticed this color became even paler at which point she was having contractions about 10 minutes apart. At this point, she went to the hospital and the baby was born 5 hours later. Her contractions were very strong only about 1 hour before delivery. |
| 3. January | Woman noted pink responses two weeks in advance (other data not available). |
| 4. May | Woman noted pink responses two weeks prior to delivery. On day of delivery color shifted to clear white at noon. Woman went to hospital at 2:00 p.m. Baby was born in evening around 6:00 p.m. |
| February | Woman monitored second pregnancy and noted color shift to pink |
| Feb. 14 | On February 28, she noted white color response at 9:00 a.m. Contractions came strong all day by baby did not come and doctor did not intervene. After two weeks baby was induced. Baby was post mature with hematoma. Diagnosis was that baby's head was in wrong position to allow for spontaneous birth. |
| 5. June | Woman showed pink color response beginning 2 weeks prior to delivery. She used test to maximize her maternity leave from work and went to work everyday until her delivery. On the day of her delivery she noted a clear reading at 9:00 a.m. She went into labor at 2:00 p.m. and the baby was born that evening at about 9:00 p.m. |

From these examples it can be seen that there are significant, easy to interpret optical changes that occur when anthocyanin pigment comes in contact with body fluids that have changes in solubility levels for estrogen concentrations. This method to assess changes in "free" estrogen solubility involve simple and accurate techniques that are easy and inexpensive and require little time. The system can be applied to many different situations that can be used in clinics, homes, farms and zoos where current technology to measure equivalent estrogen levels would not be practical or available. Furthermore, this non-invasive simple to use method has broad applications for evaluating estrogen physiological changes that occur in many animals in particular mammals and more particularly in females.

What is claimed:

1. A method for determining the unsaturated binding capacity of a body fluid from an animal to absorb free estrogen, comprising the steps of:

(a) providing a device comprising a marker system comprising an anthocyanin pigment having a concentration of $5 \times 10^{-5}$ molar to $1 \times 10^{-3}$ molar and a pH of 5.5 to 7.5, wherein said anthocyanin pigment has the formula

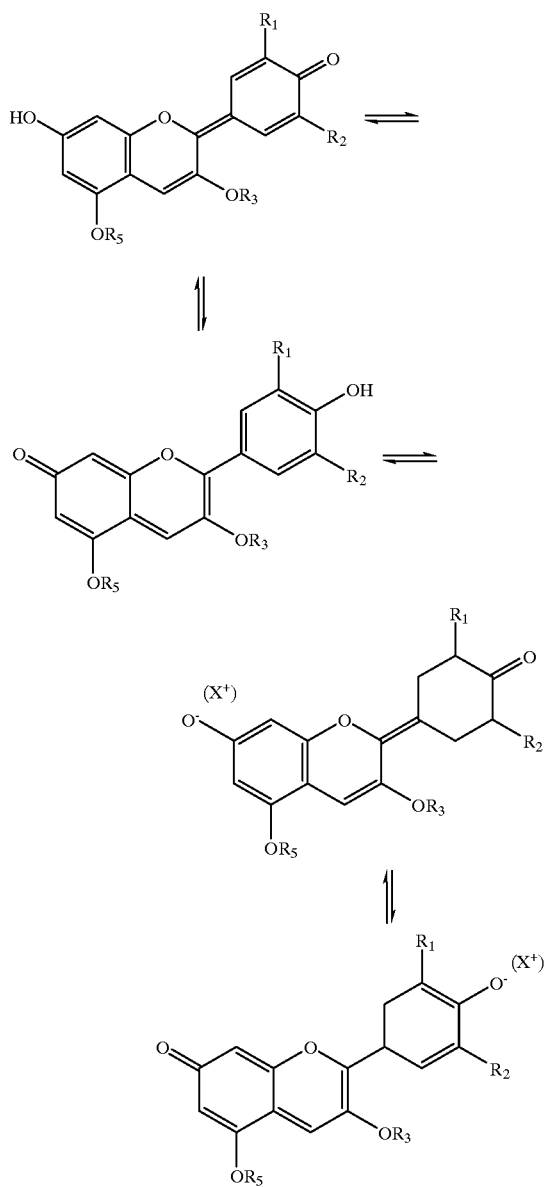

wherein $R_1$ is selected from the group consisting of hydrogen and $C_1$–$C_4$ alkoxy; $R_2$ is selected from the group consisting of hydrogen, hydroxy, and $C_1$–$C_4$ alkoxy; and $R_3$ and $R_5$ are glucosides;

(b) contacting body fluid with the marker system in the presence of a calcium salt;

(c) observing an optical color response of the marker system, wherein a blue response indicates that the body fluid has saturated its ability to absorb free estrogen and wherein a colorless to purple color response indicates the body fluid can absorb additional free estrogen and if the body fluid has unsaturated free estrogen binding capacity; and (d) determining the amount of additional free estrogen the body fluid can absorb by adding defined amounts of free estrogen to the body fluid and repeating steps (a)–(c) until a blue color response is obtained.

2. Method according to claim 1 wherein the additional free estrogen added in step (d) is 17-beta estradiol.

3. Method according to claim 1 wherein said body fluid has or is adjusted to have a pH between 5.8 and 7.2 prior to contacting the marker system.

4. Method according to claim 1 wherein the anthocyanin pigment is provided on a substrate by coating a methanol solution of the anthocyanin pigment in a concentration ranging between $5 \times 10^{-5}$ molar to $1 \times 10^{-3}$ molar and a pH of 5.8 to 7.2 on the substrate and evaporating the methanol solvent.

5. Method according to claim 1 wherein body fluid is saliva.

6. Method according to claim 1 wherein body fluid is serum.

7. Method according to claim 1 wherein body fluid is interstitial fluid.

8. Method according to claim 1 where the body fluid is maintained in a temperature range between 40 degrees Fahrenheit and 90 degrees Fahrenheit while contacting the marker system.

9. Method according to claim 1 where the substrate is selected from the group consisting of acetate, glass, acrylic, and polyethylene.

10. Method according to claim 1 where the animal is a mammal.

11. Method according to claim 10 where the mammal is female.

12. Method according to claim 11 where the female is human.

13. Method according to claim 10 where said female is an ungulate.

14. Method according to claim 10 where said female is an equine.

15. Method according to claim 1 where the calcium salt is in a solution of between $1 \times 10^{-2}$ molar and $1 \times 10^{-3}$ molar.

16. Method according to claim 1 where the anthocyanin pigment is malividin 3,5 diglucoside.

17. Method according to claim 1 where the anthocyanin pigment is petuidin 3,5 diglucoside.

18. Method according to claim 1 where the anthocyanin pigment is pelagorian 3,5 diglucoside.

19. Method according to claim 1 wherein said optical color response is measured spectrophotometrically in a wavelength range between 500 and 650 nm.

20. Method according to claim 19 where the optical density is measured in the wavelength range between 560 and 580 nm.

* * * * *